United States Patent
Amminger et al.

(10) Patent No.: US 10,314,805 B2
(45) Date of Patent: *Jun. 11, 2019

(54) PREVENTION OF PSYCHOTIC DISORDERS AND/OR TREATMENT OF PSYCHOTIC SYMPTOMS

(71) Applicant: Orygen Youth Health Research Centre, Parkville, Victoria (AU)

(72) Inventors: Gunter Paul Amminger, Vienna (AT); Patrick Dennistoun McGorry, Parkville (AU)

(73) Assignee: Orygen Youth Health Research Centre, Parkville, Victoria (AU)

( * ) Notice: Subject to any disclaimer, the term of this patent is extended or adjusted under 35 U.S.C. 154(b) by 0 days.

This patent is subject to a terminal disclaimer.

(21) Appl. No.: 15/844,444

(22) Filed: Dec. 15, 2017

(65) Prior Publication Data

US 2018/0104209 A1   Apr. 19, 2018

Related U.S. Application Data

(63) Continuation of application No. 14/269,496, filed on May 5, 2014, now Pat. No. 9,884,034, which is a continuation of application No. 13/063,035, filed as application No. PCT/AU2008/001337 on Sep. 9, 2008, now abandoned.

(51) Int. Cl.
  *A61K 31/202*  (2006.01)
  *A61K 31/232*  (2006.01)

(52) U.S. Cl.
  CPC .......... *A61K 31/202* (2013.01); *A61K 31/232* (2013.01)

(58) Field of Classification Search
  CPC .................... A61K 31/202; A61K 31/232
  See application file for complete search history.

(56) References Cited

U.S. PATENT DOCUMENTS

| | | | |
|---|---|---|---|
| 4,977,187 | A | 12/1990 | Horrobin |
| 6,852,870 | B2 | 2/2005 | Stoll |
| 2003/0045578 | A1 | 3/2003 | Horrobin |
| 2005/0113449 | A1 | 5/2005 | Renshaw |
| 2007/0141138 | A1 | 6/2007 | Feuerstein et al. |

FOREIGN PATENT DOCUMENTS

| | | | |
|---|---|---|---|
| WO | 2000044361 | A2 | 8/2000 |
| WO | 2001049282 | A2 | 7/2001 |
| WO | 2005070411 | A1 | 8/2005 |
| WO | 2007075841 | A1 | 7/2007 |

OTHER PUBLICATIONS

Allen, M. et al., Similar Rates of Agitation, Anxiety and Insomina in Sedating and Non-Sedating Antipsychotics: Evaluating Clinical Trial Results with Aripiprazole, Haloperidol and Olanzapine, Schizophrenia Res 2007: 33:418.

Amminger, G. et al., Early-onset of Symptoms Predicts Conversion to Non-Affective Psychosis in Ultra-High Risk Individuals, Schizophrenia Research, 2006, vol. 84, pp. 67-76.

Amminger, G. et al., Omega-3 Fatty Acids Reduce the Risk of Early Transition to Psychosis in Ultra-High Risk Individuals: A Double-Blind Randomized,Placebo-Controlled Treatment Study, International Congress on Schizophrenia Research, (2007) 33:418-419, Abstract.

Amminger, G. et al.,Long-Chain w-3 Fatty Acids for Indicated Prevention of Psychotic Disorder, Arch Gen Psychiatry, (2010) 67(2):146-154.

Berger. G.E., et al., Ethyl-Eicosapentaenoic Acid in First-Episode Psychosis: A Randomized, Placebo-Controlled Trial, Journal of Clinical Psychiatry, (2007) 68(12): 1867-1875.

Fenton, W.S. A Placebo-Controlled Trial of Omega-3 Fatty Acid (Ethyl-Eicosapentaenoic Acid) Supplementation for Residual Symptoms and Cognitive Impairment in Schizophrenia, American Journal of Psychiatry (2001) 158(12):2071-2074.

Kidd, P.M., Omega-3 DHA and EPA for Cognition, Behavior, and Mood: Clinical Findings and Structural-Functional Synergies with Cell Membrane Phospholipids, Alternative Medicine Review, (2007) 12(3): 207-227.

Ross, B.M. et al., Omega-3 Fatty Acids as Treatments for Mental Illness: Which Disorder and Which Fatty Acid?, Lipids in Health and Disease (2007) 6(21):1-19.

Ruxton, C. et al., The Health Benefits of Omega-3 Polyunsaturated Fatty Acids: a Review of the Evidence, J. Hum Nutr Dietet, (2007), 20:275-285.

Surette, M.E., The Science Behind Dietary Omega-3 Fatty Acids, CMAJ, (2008), 178(2): 177-180.

Posakony et al., Journal of Medicinal Chemistry, 2004, American Chemical Society, vol. 47, pp. 2635-2644.

Xiong et. al., Bioorganic and Medicinal Chemistry, 2001, Pergamon, vol. 9, pp. 1773-1780.

Larsen et al., Acta Psychiatrica Scandinavica, 2001, Munksgaard, vol. 103, pp. 323-334.

*Primary Examiner* — Sarah Pihonak
(74) *Attorney, Agent, or Firm* — Linda B. Huber; Nixon Peabody LLP

(57) ABSTRACT

The present invention relates to methods of preventing a psychotic disorder in a subject in need of intervention including administering to the subject a composition including EPA (eicosapentanoic acid) and DHA (docosahexaenoic acid). Methods of treating pre-psychotic symptoms in a subject, including administering to the subject a composition including EPA and DHA are also included.

19 Claims, 4 Drawing Sheets

(A)

(B)

PREVENTION OF PSYCHOTIC DISORDERS AND/OR TREATMENT OF PSYCHOTIC SYMPTOMS

CROSS-REFERENCE TO RELATED APPLICATIONS

This application is a continuation of U.S. patent application Ser. No. 14/269,496 filed May 5, 2014, which is a continuation of U.S. Ser. No. 13/063,035, filed Mar. 9, 2011, now abandoned, which is the National Phase of International Application PCT/AU2008/001337, filed Sep. 9, 2008, which designated the United States and that International Application was published under PCT Article 12(2) in English, the entirety of which is hereby incorporated by reference.

FIELD OF THE INVENTION

The invention is directed toward methods of prevention of psychotic disorders, including schizophrenia, in particular, inhibiting such disorders from developing.

BACKGROUND OF THE INVENTION

Psychotic disorders are a group of serious mental illnesses with an average age of onset in late adolescence or early adulthood. The most common psychotic, disorders include schizophrenia, bipolar disorder with psychotic features, major depression with psychotic features. Psychotic disorders are primarily characterized by the presence of hallucinations, delusions (such as hearing voices and paranoia) and related changes in behaviour.

Schizophrenia represents the majority of psychotic disorders (about 80%). In 1990, Schizophrenia was estimated to be the 10th leading cause of non-fatal burden in the world, accounting for 2.6% of total "years of life lived with disability" (YLD), around the same percentage as congenital malformations. The Global Burden of Disease 2000 study found the disease to be the 7th leading cause of YLDs at the global level, accounting for 2.8% of total global YLD.

Whilst the potential benefit of preventing psychotic disorders is great, currently available strategies for prevention by treating attenuated symptoms with pharmacological psychiatric interventions (e.g., antipsychotics, antidepressants, mood stabilizers) are not ideal.

Previous trials have investigated the preventive use of antipsychotic medications in ultra-high-risk groups. One study for example showed that a combination of risperidone and cognitive therapy for 8 months was significantly more effective than supportive counselling at end of intervention, but not at 12-month follow-up. A second study, compared 12 months intervention with olanzapine to placebo and found no significant intervention group differences. It was concluded that the benefits of pre-onset intervention with antipsychotics may outweigh the risks to a degree sufficient to endorse future trials. However, the use or antipsychotic medication for indicated prevention remains controversial even in research settings because of the high number of false positives (about 70-80% of people who meet ultra-high-risk criteria do not progress to psychotic disorder within one year). Somatization associated with the use antipsychotics, and unwanted side effects which include metabolic changes, sexual dysfunction and weight gain are often not acceptable. Other side effects may include dyslipidaemia, cardiac arrhythmia and osteoporosis.

The use of such medication as a preventative therapy is controversial because there is no certainty that patients at risk of developing the psychosis will go or) to develop the disease. Many patients fail to respond to these medications or only to a limited degree. None of these available medicines reliably produce a complete remission of symptoms.

The diagnostic criteria used to identify individuals at risk for psychotic disorders is imprecise, particularly given that not all individuals assessed at high risk will transition to a psychotic disorder within one year. The transition rate for individuals may vary between 5%-40% depending on the population which the risk is assessed against. Therefore pharmacological interventions are not ideal since not all individuals may benefit in the long term and would also lead to unnecessary costs and waste of resources.

In order to lower the risk of individuals transitioning to psychosis or a psychotic disorder, intervention therapies are needed. There is also a need for intervention therapies that reduce or minimise biological or psychosocial damage that manifests during the onset of psychotic disorders. There is also a need for preventative therapies with minimal risk of unwanted side-effects and also with a sustained therapeutic effect.

In contrast, omega-3 polyunsaturated fatty acids (PUPA) have been shown to be very safe even when used in relatively high doses and except from gastrointestinal symptoms like fishy eructation, nausea and loose stools which may occur, they are free of clinically relevant side effects. They have the advantage of excellent tolerability, public acceptance, relatively low costs, and benefits for general health.

Some therapeutic effects of omega-3 PUFA on cardiovascular diseases are already well known. It has also been suggested that these PUFAs are essential for normal pre-natal of post-natal development of retina and the brain.

U.S. Pat. No. 6,384,077 (Peet et al) describes a method of treating schizophrenia and related disorders in patients diagnosed as already having the disorder by administration of highly purified eicosapentanoic acid (EPA) in combination with a drug that acts primarily on neurotransmitter metabolism of receptors. The composition used in this method contains at least 90% or more EPA, and less than 5% docosahexaenoic acid (DHA).

US 2007/0161705 (Bruzzese) describes use of omega-3 PUFA, including a mixture of DHA and EPA for prevention and/or treatment, of disturbances of the central nervous system including schizophrenia.

Although it is known to a certain degree that compositions comprising combinations of omega-3 PUFA may have shown effectiveness in the treatment of mental disorders, none of the literature provide a reasonable expectation that the use of such omega-3 fatty acids may prevent or delay the onset of such diseases in individuals assessed at ultra high risk of developing a psychotic disorder. Moreover, there is no published evidence that such treatment could have long term benefits for certain individuals, after the treatment or intervention has ceased.

The present invention seeks to at least minimise one of the above limitations and/or address these needs.

SUMMARY OF THE INVENTION

In one aspect, there is provided a method of preventing a psychotic disorder in a subject in need of intervention including administering to the subject a composition including EPA (eicosapentanoic acid) and DHA (docosahexaenoic acid).

In another aspect, the present invention also provides a method of preventing a psychotic disorder in a subject including the steps of:

assessing the subject for risk of developing a psychotic disorder;

selecting subjects that meet the Ultra High Risk (UHR) criteria for developing a psychotic disorder; and administering to the selected subject a composition including EPA and DHA.

In a further aspect, the invention provides a method of treating pre-psychotic symptoms in a subject including administering to the subject a composition including EPA and DHA.

Preferably the composition is administered for a defined period, preferably for at least about 3 months up to about 8 months.

In another aspect, the present invention provides use of a composition including EPA and DHA for the preparation of a medicament for preventing a psychotic disorder in a subject in need of intervention.

In a further aspect the present invention provides use of a composition including EPA and DMA for the preparation of a medicament for treating pre-psychotic symptoms in a subject.

In yet a further aspect, the present invention provides a composition including EPA and DHA when used for the prevention of a psychotic disorder in a subject in need of intervention.

In another aspect the present invention provides a composition including EPA and DHA when used for the treatment of pre-psychotic symptoms in a subject.

In yet a further aspect, there is provided a kit for preventing a psychotic disorder including a composition including EPA and DHA and instructions for use of the kit.

In another aspect, the present invention provides a kit for treating pre-psychotic symptoms inducting a composition including EPA and DHA and instructions for use of the kit.

DETAILED DESCRIPTION

Figure 1:
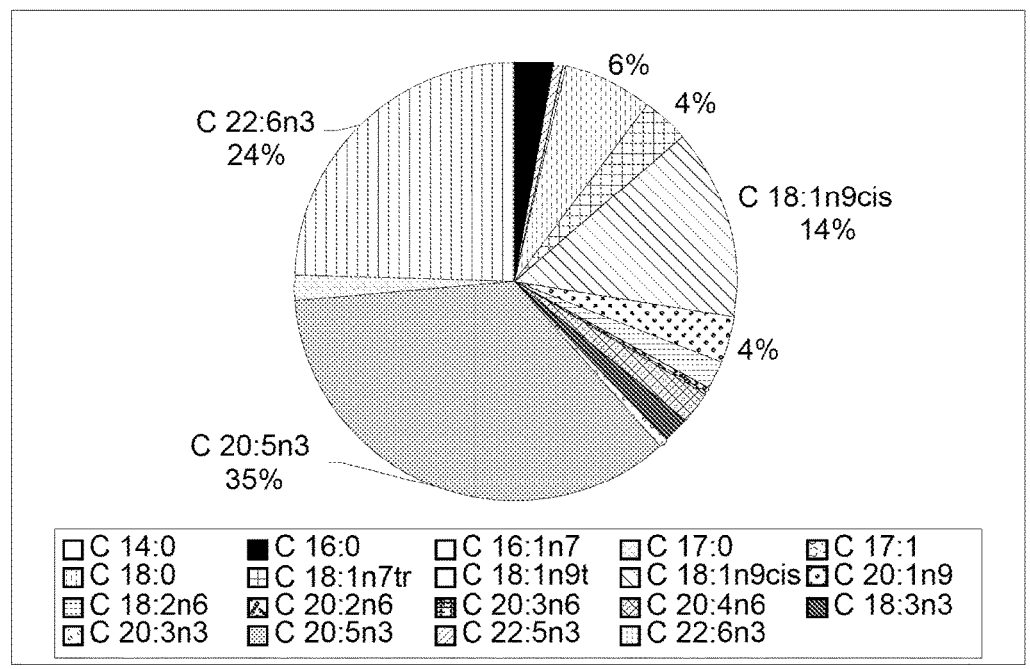
FIG. 1 Pie graphs showing fatty acid component of (A) active capsules and (B) placebo capsules used in the study of the example.
Figure 1:
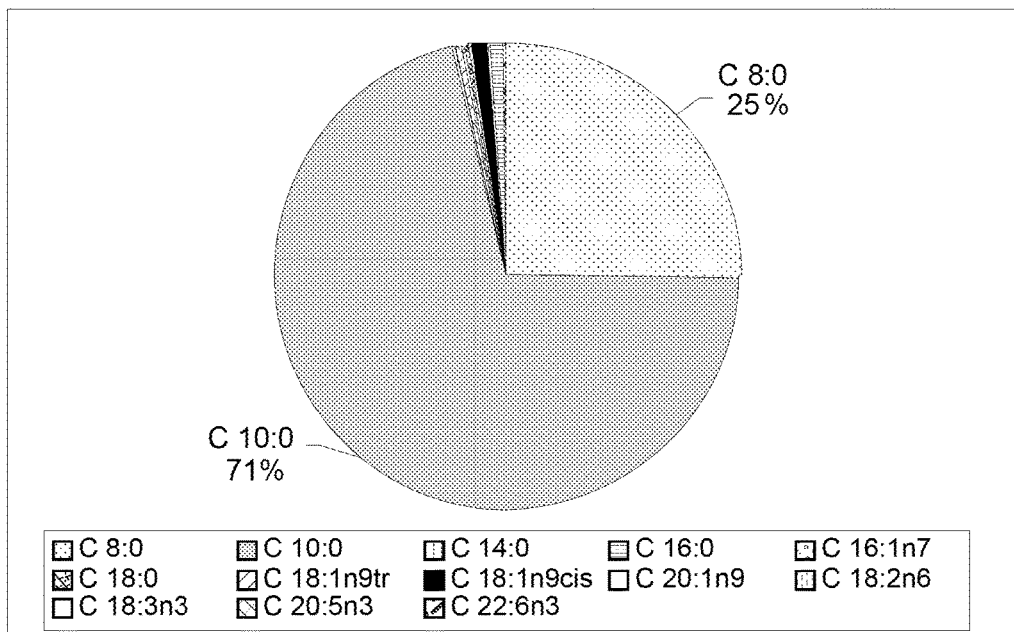

The inventors) have found that following administration of a composition including eicosapentanoic acid (EPA) and docosahexaenoic acid (DHA) over a defined period in ultra high risk (UHR) individuals, the conversion rate to psychosis for those individuals receiving the composition was significantly lower than those individuals receiving a placebo at the end of this period.

Unexpectedly, when the same group of individuals were followed up at intervals after the end of intervention, the rate of conversion to psychosis was still significantly lower in the group that received the omega-3 fatty acid composition compared to the placebo group. Thus a sustained effect from the intervention was observed in the group of UHR individuals who received polyunsaturated tatty acids (PUFA) compared to placebo beyond the period of intervention. Furthermore, the individuals who received the omega-3 fatty acid composition showed significantly reduced symptoms and improved functioning, beyond the intervention period, which was again unexpected.

The finding that the risk of individuals developing a psychotic disorder may be significantly reduced in those individuals assessed to be at ultra high risk of developing a psychotic disorder is significant. This finding therefore provides a potential for a positive outcome for those individuals without the stigma and associated side-effects with available medications.

The most striking finding by the inventors is that group differences were sustained after cessation of the intervention. Thais of antipsychotics have not found this. Without being bound by any theory or mode of action, the sustained effect may be explained by neuroprotective properties as omega-3 PUFA can induce antiapoptotic and antioxidative factors. In support of this, in vivo $^1$H-MRS has demonstrated that EPA can increase glutathione in temporal lobes of first-episode psychosis patients, which may protect neurons from oxidative stress.

In one aspect of the invention there is provided a method of preventing a psychotic disorder in a subject in need of intervention including administering to the subject a composition including EPA and DHA.

Psychotic disorders are primarily characterized by the presence of hallucinations, delusions (such as hearing voices and paranoia) and related changes in behaviour. These disorders are comprised of a group of serious illnesses of unknown aetiology, with an average age of onset in late adolescence or early adulthood, and a lifetime prevalence of 3-5%. Schizophrenia schizoaffective disorder or schizotypal disorders represent the largest group of psychotic disorders (about 80%). Other forms of psychotic disorders include for example affective psychosis, bipolar disorder with psychotic features, major depression with psychotic features.

Schizophrenia is a severe mental disorder which usually starts in adolescence or early adult life and often has a chronic disabling course. It is generally characterized by fundamental and characteristic distortions in form and content of thinking and perception (loosening of associations, delusions, and hallucinations), mood (flattened, inappropriate, or blunted affect) and behaviour (bizarre, apparently purposeless and stereotyped activity or inactivity).

Psychotic disorders, in particular schizophrenia, may be caused by a combination of genetic or biological predisposition as well as other factors such as prepregnancy factory pregnancy stress, other prenatal factors, social stress, family stress or environmental stressors during a person's life. Schizophrenia has also been associated with a chemical imbalance in the brain, involving dysregulation of the dopaminergic and serotinergic neurotransmitter systems.

In this invention, the subject in need of intervention is an individual diagnosed or assessed to be at "Ultra High Risk" (UHR) of developing or transitioning to a psychotic disorder, in particular, a psychotic disorder within 12 months from commencement of treatment.

Assessment of individuals to be at "ultra-high-risk" (UHR) of developing or transitioning to a psychotic disorder uses a combination of trait and state risk factors. The UHR criteria identify individuals with attenuated psychotic symptoms with a risk of developing psychosis within 12 months of the assessment.

Assessment may be determined using international diagnostic criteria (such as those contained in the DSM IV or the ICD 10) to interpret the results of structured or unstructured interviews (e.g. Structured Clinical Interview SCID for DSM IV). These criteria are used to distinguish between subthreshold and full threshold psychotic disorders. DSM IV classification system is otherwise known as the Diagnostic and Statistical Manual of Mental Disorders (DSM) is a widely used handbook amongst mental health professionals for diagnosing and categorising mental disorders.

UHR individuals may be assessed as having met criteria for one or more of the following three defined groups for risk factors for psychosis (also summarised in Table 1 below):

(1) attenuated positive psychotic symptoms;
(2) transient psychosis; and
(3) genetic risk plus decrease in functioning.

These individuals are also referred to as showing pre-psychotic symptoms.

The symptoms of psychotic disorders are diverse, encompassing almost every aspect of cognition and behaviour and may be characterized as positive or negative symptoms. Positive symptoms are those that are brought on by the disorder (e.g. hallucinations, delusions). Negative symptoms are those qualities taken away by the illness (e.g. one's drive and motivation are gone). These symptoms may be scored according to the Positive and Negative Syndrome Scale (PANSS). PANSS is a medical scale used for measuring symptom severity of patients with schizophrenia. It is widely used in the study of antipsychotic therapy. The name refers to the two types of symptoms in schizophrenia, as defined by the American Psychiatric Association: positive symptoms, which refer to an excess or distortion of normal functions, and negative symptoms, which represent a diminution or loss of normal functions.

The PANSS contains 30 symptoms (7 positive, 7 negative and 18 global) which are rated on scale 0=absent to 6=extreme).

The individuals assessed as being at UHR are preferably young. Young individuals are considered to be between the ages of about 13 and about 25 years of age.

In this specification, prevention or preventing or grammatical variations of this term means arresting the development of symptoms in individuals assessed to be at UHR for developing a psychotic disorder, in this specification, the terms inhibition and prevention may be used interchangeably intervention or intervening in this instance, is for the purpose of inhibiting a psychotic disorder from occurring by reducing the seventy of a psychotic disorder subthreshold manifestation of psychosis.

Prevention is considered to be successful if first episode psychosis (FEP) has not occurred for an extended period following the intervention period, preferably 1 year (or about 12 months) following the beginning of the intervention period.

The composition is administered to a subject in need of intervention for a limited period. Preferably the period of administration is between about 3 months up to about 8 months. Most preferably, the administration is for about 3 months. This period is referred to as the "intervention period". Although the intervention period (or period of administration) is for a defined period, it is also contemplated that these patients may continue administration of the composition beyond the intervention period. This may be continued indefinitely.

Once the intervention period has ceased, the individual may be continually monitored for any progression or regression of symptoms.

In another aspect, the present invention also provides a method of preventing a psychotic disorder in a subject including the steps of:

assessing the subject for risk of developing a psychotic disorder;

selecting subjects that meet the Ultra High Risk (UHR) criteria for developing a psychotic disorder; and administering to the selected subject a composition including EPA and DHA.

In yet a further aspect, the present invention provides use of a composition including EPA and DHA for the preparation of a medicament for preventing a psychotic disorder in a subject in need of intervention.

Young individuals diagnosed with attenuated psychotic symptoms at UHR for psychosis have shown structural brain abnormalities prior to their first episode psychosis (FEP), that further progress during transition to full threshold psychotic disorder, suggesting that active biological processes are involved even at this early stage of progression of the disorder. Accordingly, without being bound by any particular theory or mode of action, intervention in UHR individuals prior to FEP may reduce the risk of developing brain structural abnormalities in the patient and therefore onset of a psychotic disorder.

Psychosocial disability is also associated with psychotic disorders. Much of collateral psychosocial damage in schizophrenia is known to occur early in the pathogenesis of the disease, in particular prior to FEP. Thus before a full threshold psychotic disorder can be diagnosed significant psychosocial disability will have accrued to the individual including loss of function in the workplace or educational arena, (lose peer group school earner professional relationships) and destruction of social networks. Individuals assessed at UHR for psychosis (or subthreshold psychosis) are often severely distressed by their symptoms and there is a high risk of suicide in this group. Accordingly, without being bound by any particular theory or mode of action, intervention in UHR individuals prior to FEP may reduce the severity of psychosocial disability and consequences of the disability.

It is also therefore contemplated that the intervention according to the invention may be used to prevent, or delay the onset of one or more symptoms of a psychotic disorder. That is, the severity and number of symptoms which are identified in UHR individuals may be observed to have reduced or regress after the intervention period.

Accordingly, the present invention provides a method of treating pre-psychotic symptoms in a subject, including administering to the subject a composition including EPA and DHA.

In a further aspect the present invention provides use of a composition including EPA and DHA for the preparation of a medicament for treating pre-psychotic symptoms in a subject.

As described above, intervention and/or treatment according to the invention involves administration of a composition including EPA and DHA.

Without being bound by any theory or mode of action, the therapeutic effect of omega-3 PUFA may result from altered membrane fluidity and receptor response following their incorporation into cell membranes. Omega-3 PUFA may also interact with the dopaminergic and serotonergic systems. Both systems have been associated with the pathophysiology of schizophrenia. It is generally believed that glutathione, which protects neurons from excitability and oxidative stress, is abnormally low in schizophrenia. EPA may increase glutathione levels in the brain.

Accordingly, the present invention also provides a composition including EPA and DHA when used for the prevention of a psychotic disorder in a subject in need of intervention.

In another aspect, the present invention provides a composition including EPA and DHA when used for the treatment of pre-psychotic symptoms in a subject.

Omega 3 fatty acids are an important class of fatty acids, that include eicosapentanoic acid (EPA, C20:5 n-3) and docosahexaenoic acid (DHA, C22:6 n-3). EPA is a highly poly-unsaturated fatty acid (PUFA) which contains 20 carbon atoms and 5 double bonds all in the cis-configuration. The double bonds are located at position 5, 8, 11, 14 and 17. The full chemical name is all cis (or all z) 5, 8, 11, 14, 17-eicosapentanoic acid. DHA is also a PUFA which contains 22 carbon atoms and 6 double bonds all in the cis-configuration. The full chemical name is all cis (or all z) 4, 7, 10, 13, 16, 19-docosahexanoic acid.

Typically, dietary sources of DHA and EPA are derived from concentrated fish oils or other sources such as marine micro-organisms or plants. However, it is contemplated that oils used in the composition may be derived synthetically.

In this specification, reference to either DRA or EPA may include a pharmaceutical acceptable derivative thereof. For example, EPA may be in the form of ethyl-EPA, lithium EPA, mono-, di-, or triglyceride EPA or any other ester or salt of EPA, or its free form of EPA.

Preferably, the unit dosage form of EPA and DHA in the composition includes about 100 to 1000 mg. Preferably the composition includes about 700 mg of EPA and at least about 480 mg of DHA.

The composition is preferably formulated in a unit dosage form by well known methods. The term "unit dosage form" refers to physically discrete units suitable as unitary dosage for the subject, each unit containing a predetermined quantify of active material calculated to produce the desired effect. The final unit dosage form depends in part to the availability of suitable EPA and DHA in suitable concentrations or purity.

In a preferred embodiment of the invention, the final dose of EPA administered to the subject per day is about 700 mg and the final dose of DHA administered to the subject per day is 480 mg. The composition may be administered in multiple dosages over the period of the day. For example, 4 capsules may be administered over the course of the day (two m the morning and two in the evening). However, other administration (such as once daily, or twice dally) are not excluded.

Whilst it is possible that EPA and DHA be administered alone, it is preferable that they are administered together in a single composition. When in a single composition, EPA and DHA are present in a ratio of between about 3:1 and 7:5, preferably between about 3:2 and 7:5. Accordingly, preferably the composition includes EPA and DHA (when combined) in a concentration of more than about 50%, preferably more than about 55%, more preferably about 80%.

It will be appreciated that other omega-3 fatty acids may also be present in the composition, such as eicosatrienoic acid (ETA), eicsoatetraenoic acid, docosapentaenoic acid (DPA). Other fatty acids (i.e. other than omega-3 fatty acids) may also be present in the composition, for example oleic acid. However, omega-3 fatty acids will be the major component of the fatty acid content of the composition. Accordingly, preferably the composition includes omega-3 fatty acids in a concentration of at least 60% by weight of total fatty acids present in the composition. Preferably the omega-3 fatty acids are in a concentration of about 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% by weight of total fatty acids.

The composition may further include a pharmaceutical acceptable carrier, diluent, adjuvant and/or excipient. Each carrier, diluent, adjuvant and/or excipient must be pharmaceutically acceptable such that if is compatible with any other ingredients in the composition and not be injurious to the subject. The use of such carriers, diluents, adjuvants and/or excipients are well known in the art. Supplementary active agents may also be incorporated into the composition. Stabilizer agents or antioxidants may also be included in the composition. Preferably the composition includes Vitamin E.

The composition may be conveniently presented in a unit dosage form and may be prepared by well known pharmacological methods.

The composition is typically administered orally in the form of soft gel capsules. However, other routes of administration (such as topical or as a suppository) are not excluded. Other forms of the composition (such as a syrup, dragee, tablets etc) are not excluded.

It will be understood that the invention disclosed and defined in this specification extends to all alternative combinations of two or more of the individual features mentioned or evident from the text or drawings. All of these different combinations constitute venous alternative aspects of the invention.

EXAMPLE

The following study determined that omega-3 PUFA (EPA/DHA) can reduce psychiatric symptoms and improve psychosocial functioning in UHR individuals preventing a first episode of a psychotic disorder.

Participants

Individuals were eligible for participation if they were aged 13 to 25 years and met criteria for one or more of three operationally defined groups of risk factors for psychosis: attenuated positive psychotic symptoms; transient psychosis; and genetic risk plus a decrease in functioning (Table 1). These criteria comprise a combination of trait and state factors which identify people whose risk of becoming psychotic may approach 40% within a 12-month period. These individuals are assessed as being in an Ultra High Risk category for developing a psychotic disorder. These individuals are also referred to as showing pre-psychotic symptoms.

TABLE 1

Inclusion criteria

Group 1: Attenuated psychotic symptoms

Presence of symptom scores of 3 on the PANSS delusions scale, 2-3 on the PANSS hallucinations scale, 3-4 on PANSS suspiciousness or 3-4 on PANSS conceptual disorganisation scale (frequency of symptoms ≥2 times per week for a period of at least a week and not longer than 5 years, and have occurred within the last year).

Group 2: Transient psychosis

Presence of symptoms scores of ≥4 on PANSS hallucinations scale, ≥4 on PANSS delusions scale, or ≥5 on PANSS conceptual disorganizations scale (symptoms not sustained beyond a week and resolve without antipsychotic medication, and have occurred within the last year).

Group 3: Trait plus state risk factors

Having a schizotypal personality disorder (as defined by DSM-IV) or a first-degree relative with a DSM-IV psychotic disorder and a significant decrease in functioning resulting in a decrease of 30% on the Global Assessment of Functioning Scale from premorbid level, maintained for at least a month and not longer than 5 years. The decrease in functioning needed to have occurred within the past year.

PANSS = Positive and Negative Syndromes of Schizophrenia Scale.
DSM-IV = Diagnostic and Statistical Manual of Mental Disorders Exclusion criteria included (1) a history of a previous psychotic or manic episode, (2) substance induced psychotic disorder at index presentation, (3) acute suicidal or aggressive behaviour, (4) drug or alcohol abuse that contributed decisively to the index presentation (e.g., dependency on morphine, cocaine, amphetamine, but not cannabis), (5) neurological disorder, (6) IQ<70, (7) structural brain changes in MRI scan (e.g., tumours), except for enlargement of ventricles or sulci, (8) previous treatment with an antipsychotic or mood stabilizing agent (>1 week), (9) taken omega-3 supplements within 8 weeks of being included in the trial, (10) laboratory values more than 10% outside the normal range for transaminases, thyroid hormones, CRP or bleeding parameters, (11) another, severe, intercurrent illness which may put the person at risk or influence the results of the trial or affect ability to take part in the trial.

Study Design

A randomised, double-blind, placebo-controlled 12-week intervention trial of 1.2 g per day omega-3 PUFA was undertaken. After randomisation, participants received weekly assessments for 4 weeks, and then at 8, 12 weeks, 6, and 12 months. A computer-generated random sequence based on a block randomised design was administered by an independent third party until all study data were collected. Participants, parents, and those involved in study interventions, assessing outcomes, data entry and/or data analyses were blind to group assignments. The study was carried out at the psychosis detection unit of the Department of Child and Adolescent Psychiatry, Medical University of Vienna (MUW), Austria. All consecutive, referrals between April 2004 and May 2006 were considered for inclusion. The study was approved by the MUW ethics committee (EK-Nr.415/2002), and written informed consent was obtained from all participants (parental or guardian consent was obtained for those <18 years).

Study Intervention

The active treatment was a supplement of yellow gelatin 0.5 g fish oil capsules. The daily dose of 4 capsules provided 700 mg of EPA, 450 mg of DHA, and 7.6 mg of Vitamin E. The total daily dose of other omega-3 fatty acids was 220 mg. This provides a daily dose of 1.2 g omega-3 PUFA. Coconut oil was chosen as placebo because it does not contain polyunsaturated fatty acids and has no impact on omega-3 fatty acid metabolism. Placebo capsules were carefully matched in appearance and flavour with the active treatment. The placebo capsules also contained 10 mg Vitamin E; and 10 mg of fish oil to mimic taste.

The fatty acid composition for the active and placebo capsules used in this study is shown in FIG. 1. The fatty acid composition in each of the capsules is outlined in Table 2:

TABLE 2

| Fish Oil capsules | | Placebo capsules | |
| --- | --- | --- | --- |
| 20:5n3 | 35% | 8:0 | 25% |
| 22:6n3 | 24% | 10:0 | 71% |
| 18:1n9 | 14% | 20:5n3 plus 22:6n3 | <1.5% |
| 18:0 | 6% | Other fatty acids combined (14:0, 16:0, 17:0, 18:0, 18:1n7t, 18:1n9t, 18:1n9c, 20:1n9, 22:1n9, 24:1n9, 18:2n6t, 18:2n6c, 18:3n6, 18:3n3, 20:3n6, 20:4n6, 22:2n6, 22:5n3, 22:6n3) | <3% |
| 18:1n7tr | 4% | | |
| 20:1n9 | 4% | | |
| 16:0 | 3% | | |
| 20:4n6 | 3% | | |
| 18:3n3 | 3% | | |
| 17:0 | 2% | | |
| 18:2n6 | 2% | | |
| 20:3n6 | 1% | | |
| Other fatty acids combined | 4% | | |

Adherence was monitored by pill count and erythrocyte fatty acid quantification. Antipsychotic medication or mood stabilizers were not permitted. Patients could receive antidepressants for moderate to severe depression, benzodiazepines for anxiety, agitation, or insomnia, and needs-based, psychosocial interventions for 12 months.

Outcome Measures

The primary efficacy endpoint was conversion to psychosis, based on operationally defined criteria using cut-off points on the Positive and Negative Syndrome Scale (PANSS)[1] (≥4 on hallucinations, ≥4 on delusions and ≥5 on conceptual disorganization), the frequency of positive symptoms (≥2 per week), and their duration (≥1 week). Secondary measures included the PANSS, the Montgomery Asberg Depression Rating Scale (MADRS)[2], and the Global Assessment of Functioning (GAF).[3] Raters were trained in administration of outcome measures and interrater reliability estimates for PANSS subscales, MADRS, and GAF were excellent (all ICC coefficients >0•92). The Structured Clinical Interview for DSM-IV-TR Axis I Disorders (SCID-I/P)[4] was used to ascertain psychiatric diagnoses at baseline and 12-month follow-up. At baseline and 12-week follow-up, fasting erythrocyte fatty acid composition was quantified using capillary gas chromatography after fatty acid extraction from washed erythrocytes. The ratio of omega-8 to omega-3 fatty acids (omega-6/omega-3) was used to index pre- vs. post-intervention fatty acid composition.[12] Intervention-emergent side effects were assessed with the Udvalg for Kliniske Undersøgelser (UKU).[5]

Statistical Analysis

The study was powered to detect a 50% reduction in the expected transition rate, corresponding to a transition rate to psychosis (over 12 months) of 20% in the omega-3 group and an anticipated rate of 40% in the placebo group. Power analysis indicated that 75 subjects would provide a 70% chance of detecting such an effect (two-sided alpha level of 0•05). Allowing for 5-10% dropout, we sought to recruit at least 80 participants.

All analyses were performed on an intent-to-treat basis. Kaplan-Meier survival analysis assessed differences in time to transition to psychosis between intervention arms at 12-month follow-up using the log-rank test. Estimated survival rates at various points on the survival curve (12-week, 6-, and 12-month) were compared using z-tests. Sensitivity analysis was also performed under the assumption that all participants who were lost to follow-up (n=5) prior to the 12-month assessment had converted to psychosis. Number needed to treat[6] was used to determine the number of individuals needed to be treated with omega-3 PUFA to prevent one individual from progressing to first-episode psychosis.

For secondary outcome measures, analyses were carried using the mixed model repeated measures analysis ANOVA (MMRM). The within groups factor was measurement occasion (T0 to T8) and medication group served as the between groups factor. A Toeplitz covariance structure was used to model relations between observations on different occasions. A series of planned comparisons contrasted change from baseline (T0) to 12-week (T6), 8-month (T7), and 12-month (T8) between omega-3 and placebo. MMRM differs from traditional repeated measures ANOVA in that all available data are included in the model and the relationships between different time points is also modelled. Analyses were undertaken using the MIXED procedure in SPSS Version 16.0.

In this trial missing secondary outcome data occurred in two distinct ways. Observations could be missing data due to withdrawal or missed assessments. These observations can reasonably be assumed to be 'missing at random'. The second type of missingness relates to data that are absent following transition to psychosis. Antipsychotic medication was commenced in participants who made the transition to psychosis and no further data were collected after transition. The outcome of interest—the values that participants would have had if active intervention for psychosis had not been initiated and the intervention and observation had continued—is effectively counterfactual. In these circumstances, missingness is not at random and must be explicitly modelled.[7] A conservative approach was taken to model post-transition outcomes, it was assumed that symptoms and functioning would have been maintained at the transition levels, if antipsychotic medications had not been administered, but would not have further increased.

Differences between intervention groups on categorical variables were analyzed using Fishers exact test. Independent-samples Rests were used to compare group differences in baseline-to-12-week omega-6/omega-3 changes in erythrocyte fatty acid composition. Correlational analysis examined associations between baseline-to-12-week omega-6/omega-3 ratio changes and secondary outcome measures.

This study is registered with ClinicalTrials.gov, number NCT00396843.

Results

Study Sample

Figure 2:
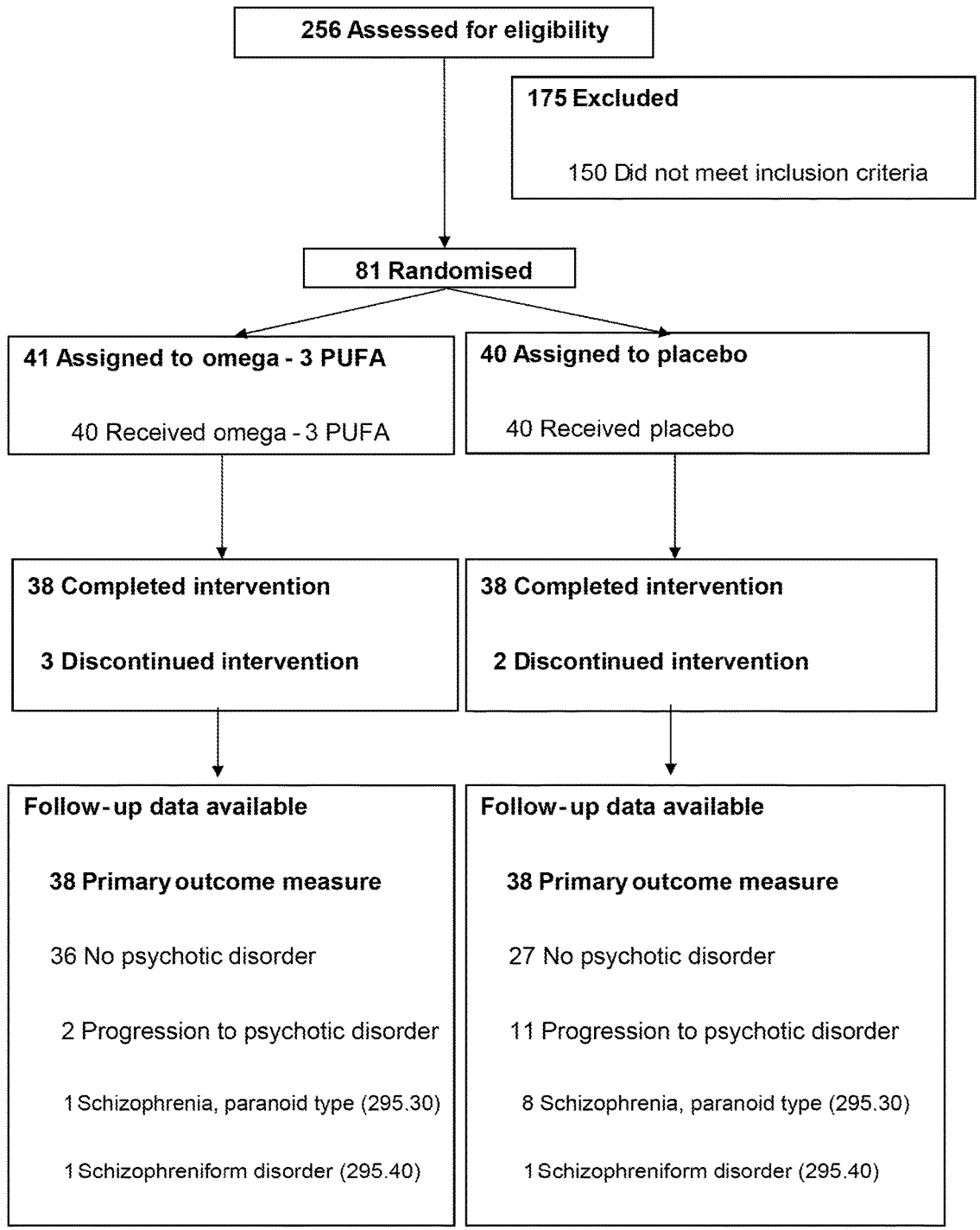
FIG. 2 Flow diagram showing enrolment, selection and outcomes of the study of the example.

Eighty-one intervention-seeking individuals were enrolled, 41 were randomly assigned to omega-3 PUFA and 40 to placebo. Both groups had comparable baseline characteristics (Table 3). Three of 41 (7•3%) patients from the omega-3 group, and 2/40 (5•0%) from the placebo group, discontinued the intervention prematurely (P=0•67). The remaining 76/81 (93•8%) patients who completed the 12-week intervention, also completed 12-month follow-up for the primary outcome or made a transition to psychosis during this period; 67/81 (82•7%) completed 12-month follow-up for secondary outcomes (FIG. 2).

TABLE 3

Baseline characteristics of participants

|  | Omega-3 (n = 41) | Placebo (n = 40) |
|---|---|---|
| Age (years) | 16.8 (2.4) | 16.0 (1.7) |
| Sex (male) | 14 (34%) | 13 (33%) |
| Body-mass index (kg/m$^2$) | 21.1 (4.2) | 21.4 (3.5) |
| Tobacco | 18 (44%) | 24 (60%) |
| Alcohol | | |
| Less than weekly | 23 (56%) | 23 (58%) |
| 1-6 drinks per week | 10 (24%) | 11 (28%) |
| Daily | 8 (20%) | 6 (15%) |
| Marijuana | | |
| No | 35 (85%) | 34 (85%) |
| Less or equal 2 gram per week | 4 (10%) | 4 (10%) |
| More than 2 gram per week | 2 (5%) | 2 (5%) |
| Any illicit drug use | 6 (15%) | 8 (20%) |
| Psychiatric medication | | |
| Antidepressant | 14 (34%) | 13 (33%) |
| Benzodiazepine/sedative | 7 (17%) | 3 (8%) |
| Entry criteria | | |
| Attenuated psychotic symptoms | 37 (90%) | 38 (95%) |
| Transient psychosis | 3 (7%) | 2 (5%) |
| Trait plus state risk factors | 4 (10%) | 2 (5%) |
| PANSS score | | |
| Total score | 59.9 (13.1) | 57.2 (13.9) |
| Positive subscale | 15.0 (3.4) | 14.2 (3.1) |
| Negative subscale | 14.1 (5.3) | 13.6 (6.5) |
| General subscale | 30.9 (7.2) | 29.4 (6.6) |
| MADRS score | 17.6 (8.9) | 18.8 (8.7) |
| GAF score | 61.0 (12.0) | 60.0 (13.1) |
| Erythrocyte fatty acids - % of total | | |
| Total saturated | 38.4 (4.1) | 38.9 (5.0) |
| Total monosaturated | 27.1 (2.6) | 27.4 (3.7) |
| Total omega-6 fatty acids | 28.8 (2.8) | 28.3 (2.5) |
| Linoleic (18:2n-6) | 6.2 (0.8) | 6.3 (1.7) |
| Arachidonic (20:4n-6) | 15.8 (2.2) | 15.3 (2.0) |
| Total omega-3 fatty acids | 5.6 (1.2) | 5.3 (1.0) |
| Eicosapentaenoic (20:5n-3) | 0.5 (0.2) | 0.5 (0.1) |
| Docosapentaenoic (22:5n-3) | 2.2 (0.4) | 2.2 (0.4) |
| Docosahexaenoic (22:6n-3) | 2.8 (0.8) | 2.5 (0.6) |
| Family history of psychosis | | |
| Psychosis | 10 (25%) | 6 (15%) |
| Non-psychotic bipolar disorder | 1 (3%) | 0 (0%) |
| Non-psychotic depression | 13 (33%) | 12 (31%) |
| Other psychiatric disorder | 11 (28%) | 6 (16%) |

Data are mean (SD) or n (%).
PANSS denotes Positive and Negative Syndrome Scale, MADRS Montgomery Asberg Depression Rating Scale, and GAF Global Assessment of Functioning.

Efficacy

Primary Outcome Measure

Figure 3:
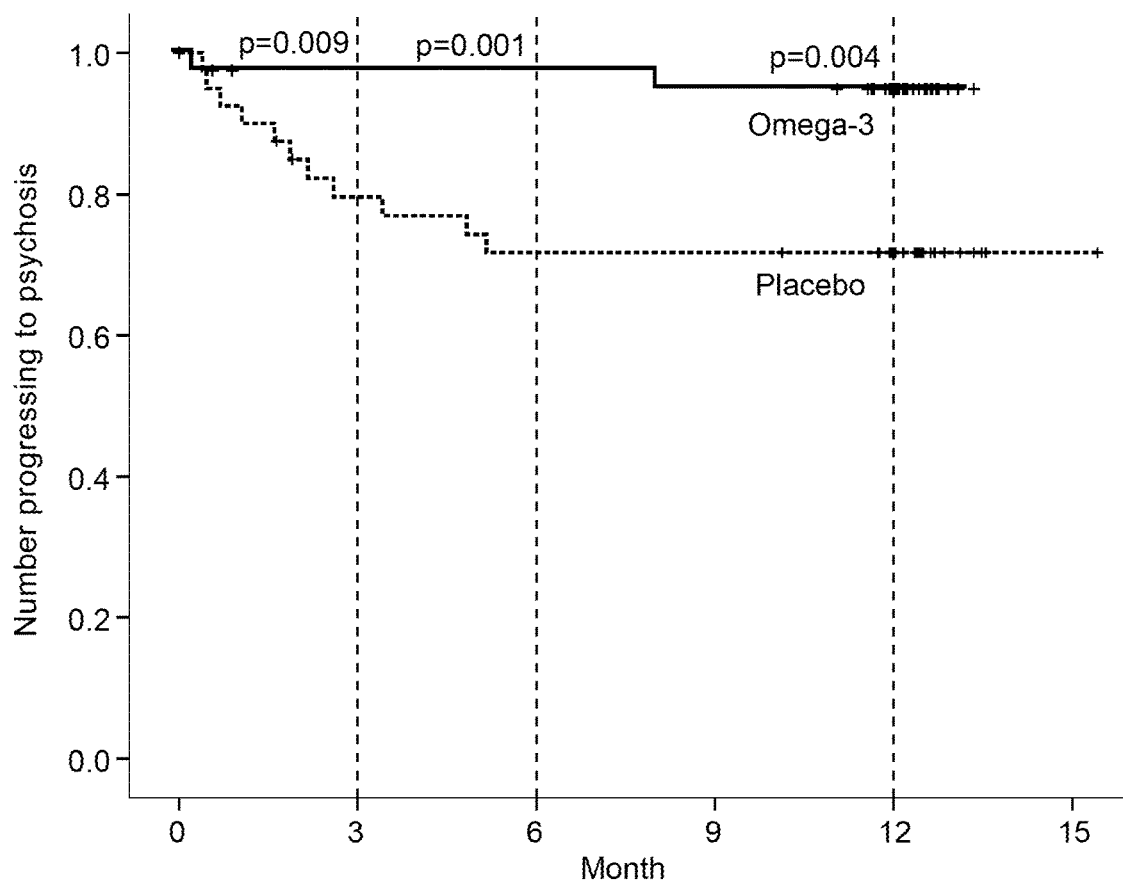
FIG. 3 Kaplan-Meier survival analysts of transition from prodromal state to psychosis in patients assigned to omega-3 fatty acids (n=41) or placebo (n=40) in the study of the example.

The cumulative conversion rate to psychosis at 12 weeks was 2•4% (1/41) for omega-3 and 20•0% (8/40) for placebo;

at 6 months the rate was 2•4% (1/41) and 27•5% (11/40), and at 12 months the rates were 4•9% (2/41) and 27•5% (11/40), respectively. The risk of progression to psychosis was significantly lower in the omega-3 group than the placebo group over the course of the study (p=0•009 at 12 weeks; p=0•001 at 6 months and p=0•004 at 12 months) (FIG. 3). By 12 months the difference between the groups in the cumulative risk of progression to psychosis was 22•6% (95% Cl 4•8 to 40•4 with continuity correction). A more rapid conversion time for the placebo group compared with the omega-3 group (log rank test $\chi^2$=7•32, p=0•007) was observed (FIG. 3). The sensitivity analysis (log rank test, $\chi^2$=4•37, p=0•037) was consistent with the intention-to-treat analysis.

Number Needed to Treat

The number needed to treat with omega-3 PUFA in the study to prevent one individual from progressing to psychosis over a 12-month period was 4 (95% Cl 3 to 14) (rounded to the nearest, whole number).

Secondary Outcome Measures

Figure 4:
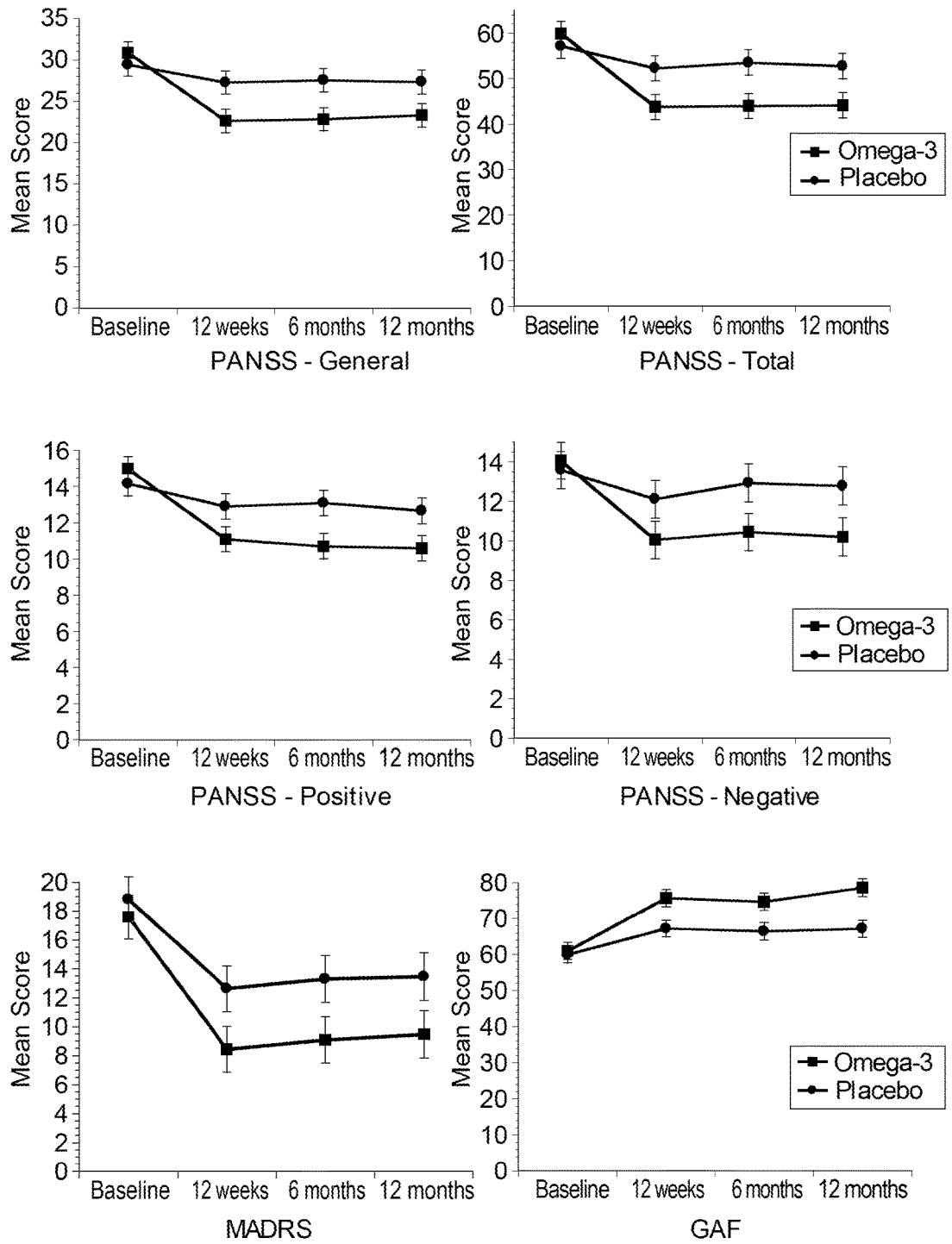
FIG. 4 shows mean scores (85% Cl) for secondary outcome measures for omega-3 fatty acids (square) and placebo (circle). Points represent means, and bars represent the 95% Cl. For the PANSS the minimum total score is 30, and the minimum score for the positive, negative, and global subscale is 7, 7, and, 16, respectively. The MADRS measures the severity of 10 symptoms on a scale from 0 to 6. The GAF measures social, occupational and psychological functioning on a single numeric scale (0 through 100), with higher scores indicating better functioning.

FIG. 4 shows mean scores (95% Cl) for secondary outcome measures. For post-transition outcomes it was conservatively assumed that symptoms and functioning would have maintained at the transition levels, if antipsychotic medications had not been administered. For the PANSS measures the omnibus interactions between medication group and occasion were not significant (positive, F[8, 163•5]=1•72, p=0.098; negative F[8, 162•0]=1•26, p=0•268; global F[8, 164•2]=1•74, p=0•093; total F[8, 152•2]=1•66, p=0•113]). This reflects the emergence of differences between the groups only later in the trial. Planned comparisons detected between group differences fit these times. The omega-3 group had significantly lower PANSS positive, negative, global and total scores, at 12 weeks, 8 months, and at 12 months as compared to the control cohort (all p<0•05). There was no significant interaction for the MADRS, and none of the planned contrasts were significant. For the GAF, there was a significant interaction between medication group and occasion, F(8, 139•8)=2•99; p=0•004. At 12 weeks (p=0•002), 6 months (p=0•023), and at 12 months (p=0•018), the omega-3 group demonstrated significantly higher functioning than the control group. Table 4 below shows changes in symptoms and functioning from baseline after 12 months.

Fatty Acids

Mean (SD) baseline-to-12-week changes in the omega-6/omega-3 ratio in erythrocytes of patients treated with omega-3 and patients given placebo were −2•0 (1•2) and −0•1 (0•7), respectively. There was a significant increase of omega-3 relative to omega-6 in the active intervention group pre- vs. post-intervention, (t=8•1, df=63•3, p<0•001). Pre- vs. post-intervention change in omega-6/omega-3 ratio was significantly associated with a decrease in PANSS global symptoms (r=0•23, p=0•04) and an increase of the GAF score (r=−0•27, p=0•02). At the 12-month follow-up, the change in omega-6/omega-3 ratio was significantly associated with an increase of the GAF score (r=0•27, p=0•03). No significant associations were observed for other measures. The results of the measurements are shown in Table 5 below.

Adverse Events

No statistically significant group differences were observed between omega-3 PUFA and placebo on the UKU (Table 6).

TABLE 5

Side effects from baseline to end-of-intervention (12 weeks)

| | Omega-3 (n = 41) | Placebo (n = 40) | P Value* |
|---|---|---|---|
| Tension/inner unrest | 4 (9.8) | 5 (12.5) | 0.737 |
| Depression | 2 (4.9) | 5 (12.5) | 0.264 |
| Concentration difficulties | 1 (2.4) | 5 (12.5) | 0.109 |
| Emotional indifference | 2 (4.9) | 4 (10.0) | 0.432 |
| Diarrhea | 1 (2.4) | 4 (10.0) | 0.201 |
| Tension headache | 1 (2.4) | 4 (10.0) | 0.201 |
| Nausea/vomiting | 3 (7.3) | 3 (7.5) | 1.0 |
| Reduced duration of sleep | 3 (7.3) | 3 (7.5) | 1.0 |
| Increased fatigability | 3 (7.3) | 2 (5.0) | 1.0 |
| Failing memory | 0 (0.0) | 2 (5.0) | 0.241 |
| Increased tendency to sweating | 0 (0.0) | 2 (5.0) | 0.241 |
| Orthostatic dizziness | 0 (0.0) | 2 (5.0) | 0.241 |

Data are number (%).
Included are side effects according to the 48-item UKU rating scale that occurred with a prevalence of ≥5% in any intervention group.
*P values were determined using Fisher's exact test.

Adherence and Concomitant Medication

Adherence with study medication (mean) was 81.4% (SD 17.7%) for the omega-3 group and 75.4% (SD 17.8%) for the placebo group (p=0•13). Concomitant medication use

TABLE 4

Changes from baseline to 12-month endpoint of secondary outcome measures

| | Baseline | | Change from baseline | | | |
|---|---|---|---|---|---|---|
| | Omega-3 (n = 41) | Placebo (n = 40) | Omega-3 (n = 41) | Placebo (n = 40) | P value* | Effect size† |
| PANSS score | | | | | | |
| Total | 59.9 (2.7) | 57.2 (2.7) | −15.7 (2.8) | −4.4 (2.8) | 0.006 | 0.70 |
| Positive | 15.0 (0.7) | 14.2 (0.7) | −4.4 (0.8) | −1.5 (0.8) | 0.010 | 0.69 |
| Negative | 14.1 (0.9) | 13.6 (0.9) | −3.9 (0.9) | −0.8 (0.9) | 0.019 | 0.52 |
| Global | 30.9 (1.4) | 29.4 (1.4) | −2.1 (1.5) | −7.5 (1.5) | 0.010 | 0.68 |
| MADRS score | 17.5 (1.5) | 18.8 (1.6) | −8.1 (1.9) | −5.3 (1.9) | 0.291 | 0.32 |
| GAF score | 61.0 (2.3) | 60.0 (2.4) | 17.7 (2.3) | 7.2 (2.3) | 0.002 | −0.72 |

Data are mean (SE).
PANSS denotes Positive and Negative Syndrome Scale,
MADRS Montgomery Asberg Depression Rating Scale, and
GAF Global Assessment of Functioning,
*P values are based on the contrasts from the repeated measures mixed models analysis.
†Difference in change from baseline in units of standard deviations of change.

after randomisation included antidepressants in 5/41 (12•2%) omega-3 patients and 3/40 (7•5%) placebo patients (p=0•48), and benzodiazepine in 2/41 (4•9%) omega-3 patient and 1/40 (2•5%) placebo patient (p=0•57).

Summary

A randomized, double-blind, placebo-controlled trial tested the efficacy of 1.2 g/day omega-3 PUFA in 81 UHR individuals. Notably, a 12-week intervention period (to test the intervention immediate effect) was followed by a 40-week monitoring period. The conversion rate to psychosis at 12 weeks follow-up (end of intervention) was 2.4% (1/41) for omega-3 and 20.0% (8/40) for placebo (p=0.009 at 12 weeks).

Unexpectedly, at 12-month follow-up, 9 months after end of intervention, the rate of conversion to psychosis was still significantly lower in the omega-3 group compared to the placebo group, 4.9% (2/41) vs. 27.5% (11/40), respectively (p=0.004 at 12 months).

In contrast to the "wash-out" effect which is typically seen when an active intervention is ceased, we unexpectedly observed a lasting, sustained intervention effect in the group of UHR individuals who received omega-3 compared to placebo beyond the period of intervention. The difference between the groups in the cumulative risk of progression to psychosis was 22.6% (95% Cl 4.8-40.4) (FIG. 2).

Furthermore, omega-3 PUFA also significantly reduced positive symptoms (p=0.006), negative symptoms (p=0.019), global symptoms (p=0.01), and improved functioning (p=0.002) compared to placebo over the total course of the study beyond the intervention period with out showing the usual wash-out effect after intervention with omega-3 was ceased, which was again unexpected (FIG. 3).

The incidence of side effects was generally low and did not differ between the intervention and placebo groups at any time over the course of the study.

Omega-3 significantly reduced the transition rate to psychosis and led to significant symptomatic and functional improvements. The magnitude of group differences ranged from moderate (negative symptoms) to moderate-to-large (positive, global and total symptoms, and GAP) (see Table 3). Only one patient on omega-3 intervention developed psychosis during the post-intervention follow-up period. Prodromal symptoms and functioning in patients who received omega-3 did not return to higher levels of severity after the intervention was stopped. These findings are consistent with a preventive, disease progression modifying intervention effect. The high consent rate (76•4%, 81/106) and the low withdrawal rate during the intervention period (6•2%, 5/81) strengthen the results and indicate that omega-3 PUFA were well received by this population.

The finding that intervention with a natural substance may prevent the onset of psychotic disorder provides a potential alternative to antipsychotics for the prodromal phase.

The present results have been obtained in the context of specific risk criteria and should not be generalised to other risk definitions. Psychosis exit criteria were based on progressive positive symptoms, thus potentially including a broader range of psychotic disorders as well as schizophrenia. Although most individuals who converted to psychosis were diagnosed with DSM-IV schizophrenia or schizophreniform disorder at 12-month follow-up (84•6%, 11/13) (see FIG. 2), the study aimed to prevent psychotic disorders in general. Strengths of the study include the randomised, placebo-controlled design, the use of standardised inclusion and exit criteria, integrator reliability testing, the application of an objective compliance measure, the observed correlation between clinical changes with erythrocyte fatty acid composition changes, the robustness of findings across multiple statistical techniques and sensitivity analysis, and last hut not least, confirmation at 12-month follow-up by means of SCID-I/P interview that all people who met exit criteria made transitions to genuine psychotic disorders.

The work described in this example was supported by Stanley Medical Research institute grant 03T-315.

REFERENCES

1. Kay S R, Fiszbein A, Opler L A. The positive and negative syndrome scale (PANSS) for schizophrenia. Schizophr Bull 1987; 13:281-76.
2. Montgomery S A, Asberg M. A new depression scale designed to be sensitive to change. Br J Psychiatry 1979; 134:382-9.
3. Diagnostic and statistical manual of mental disorders, 4th ed.; DSM-IV. Washington, D.C.: American Psychiatric Association, 1994.
4. First M B, Spitzer R L, Gibbon M, et al.; Structured Clinical interview for DSM-IV-TR Axis I Disorders, Research Version, Patient Edition. (SCID-I/P). New York, Biometrics Research, New York State Psychiatric Institute, 2002
5. Lingjaerde O, Ahlfors U G, Bech P, et al. The UKU side effect rating scale. A new comprehensive rating scale for psychotropic drugs and a cross-sectional study of side effects in neuroleptic-treated patients. Acta Psychiatr Scand Suppl 1987; 334:1100.
6. Cook R J, Sackett D L. The number needed to treat: a clinically useful measure of treatment effect. BMJ 1995; 310:452-4.
7. Henderson R, Diggle P, Dobson A. Joint modelling of longitudinal measurements and event time data. Biostatistics 2000; 1:465-80.

The invention claimed is:

1. A method of increasing functioning in a subject that meets the ultra high risk (UHR) criteria for developing a psychotic disorder including administering to the subject a composition including eicosapentanoic acid (EPA) and docosahexaenoic acid (DHA) for one or more intervention periods, wherein each intervention period is 3 to 6 months; and wherein the functioning of the subject is assessed as increased after six months and/or after 12 months from commencing an intervention period and wherein functioning remains increased 9 months after an intervention period is ceased.

2. The method according to claim 1, wherein the one or more intervention periods increases the functioning of the subject after six months and after 12 months from beginning an intervention period.

3. The method according to claim 1, wherein the increase in functioning is assessed using the Global Assessment of Functioning (GAF).

4. The method according to claim 1, wherein the subject at 12 months after commencing the administration functions at the equivalent of a 78.7 Global Assessment of Functioning (GAF) score.

5. The method according to claim 1, wherein the increase in functioning is equivalent to an increase of 17.7 in Global Assessment of Functioning (GAF) score.

6. The method according to claim 1, wherein the subject is between about 13 to 25 years of age.

7. The method according to claim 1, wherein the EPA and DHA are present in the composition in a ratio of between 3:2 to 7:5 by weight.

8. The method according to claim 7, wherein the EPA and DHA are in a concentration of more than 50% by weight of total fatty acids.

9. The method of claim 1, wherein the composition is administered to the subject such that the subject is administered a dosage of 700 mg EPA and 480 mg DHA per day.

10. The method of claim 1, wherein the total quantity dose of EPA and DHA administered per day is about 1.2 g.

11. The method according to claim 1, wherein the method further prevents or delays the subject's experience of a first episode of psychosis or the development of a psychotic disorder in the subject.

12. The method according to claim 11, wherein the psychotic disorder is schizophrenia, schizophreniform disorder, schizoaffective disorder, bipolar disorder with psychotic features or major depression with psychotic features.

13. The method of claim 1, wherein the method further reduces the risk that the subject will transition to psychosis by at least 22.6%.

14. The method of claim 1, wherein the method further reduces the severity of subthreshold manifestation of psychosis for at least 12 months after beginning an intervention period.

15. The method according to claim 1, wherein the EPA and DHA are in triglyceride form.

16. The method according to claim 1, wherein the composition is administered twice daily.

17. The method according to claim 1, wherein the composition includes vitamin E.

18. The method according to claim 1, wherein the intervention period is 6 months.

19. The method according to claim 1, wherein the composition is the only composition administered to improve functioning.

* * * * *